United States Patent [19]

Janssen et al.

[11] Patent Number: 5,041,648
[45] Date of Patent: Aug. 20, 1991

[54] PHENYLHYDRAZONES OF BETA-IONONE

[75] Inventors: Bernd Janssen, Ludwigshafen; Hans-Heiner Wuest, Dossenheim, both of Fed. Rep. of Germany

[73] Assignee: BASF Aktiengesellschaft, Ludwigshafen, Fed. Rep. of Germany

[21] Appl. No.: 468,288

[22] Filed: Jan. 22, 1990

[30] Foreign Application Priority Data

Feb. 10, 1989 [DE] Fed. Rep. of Germany ....... 3903991

[51] Int. Cl.$^5$ ................ C07C 229/60; C07C 233/65; C07C 259/10
[52] U.S. Cl. ..................................... 562/622; 558/422; 560/34; 560/315; 562/66; 562/439; 564/149; 564/251
[58] Field of Search .................. 558/422; 560/34, 315; 562/66, 439, 622; 564/149, 251

[56] References Cited

U.S. PATENT DOCUMENTS

| | | | |
|---|---|---|---|
| 2,811,558 | 10/1987 | Sannie et al. | 564/250 X |
| 2,815,379 | 12/1957 | Surmatis | 564/251 X |
| 3,742,052 | 6/1973 | Bordenca | 564/250 X |
| 3,923,506 | 12/1975 | Bergfjord et al. | 564/251 X |
| 4,326,055 | 4/1982 | Loeliger | 568/426 X |
| 4,588,750 | 5/1986 | Boris | 514/765 |

FOREIGN PATENT DOCUMENTS 2164938 4/1986 United Kingdom .

OTHER PUBLICATIONS

Journal of Medicinal Chemistry, vol. 27, No. 8, pp. 1516–1531, Aug. 1984, M. I. Dawson, et al.
The Retinoids, vol. 2, pp. 391–409, (1984), G. L. Peck, ED.: M. B. Sporn, et al., Academic Press.
The Medical Journal of Australia, vol. 146, pp. 374–377 (1987) R. Marks, et al.
The Retinoids, A Review of Their Clinical Pharmacology, Drugs vol. 34, pp. 459–503 (1987), C. E. Orfanos, et al.
Berichte, vol. 66, pp. 798–801 (1933), Pummerer, Rebmann.
Makromol. Chem. vol. 187, pp. 1573–1582 (1986), E. Lobo Filho, et al.

Primary Examiner—Richard L. Raymond
Attorney, Agent, or Firm—Oblon, Spivak, McClelland, Maier & Neustadt

[57] ABSTRACT

β-ionone pheylhydrazones of the formula I

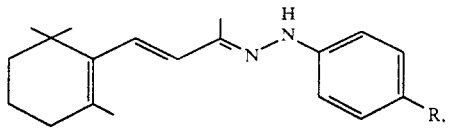

where R has the meaning indicated in the description, and the preparation thereof are described. The substances are suitable or controlling diseases and as cosmetic agents.

3 Claims, No Drawings

PHENYLHYDRAZONES OF BETA-IONONE

It has been disclosed that retinoic acid derivatives (cf. M. J. Dawson et al., J. Med. Chem. 27, (1984) 1516–31) and stilbene derivatives (cf. U.S. Pat. No. 4,326,055, GB 2,164,938 and U.S. Pat. No. 4,588,750) in which the polyene structure of substances of the vitamin A type is immobilized in aromatic rings display pharmacological effects in vitro and in vivo experimental models and on the topical and systemic therapy of neoplasms acne, psoriasis and other dermatological disorders. However, the effect of these compounds is still unsatisfactory (cf. G. L. Peck in: The Retinoids, Vol. II, 391–409, Ed.: M. B. Sporn et al., Academic Press N.Y. (1984) or R. Marks et al., Med J. Australia 146 (1987) 374–377 or C. E. Orfanos et al., Drugs 34 (1987)-459–503).

Hence the object of the present invention was to develop compounds with an improved spectrum of action.

We have now found, surprisingly, that the phenylhydrazones of the formula I

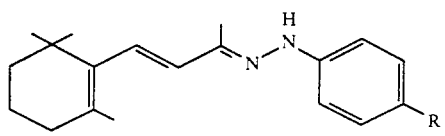

where R is hydrogen, nitro, $C_1$–$C_4$-alkoxy or -alkyl, cyano, sulfo, or —$CONH_2$, —$CO_2R^1$ or —$S(O)_nR^2$ (with n=0 or 2) where $R^1$ is hydrogen or $C_1$–$C_3$-alkyl, and $R^2$ is $C_1$–$C_3$-alkyl and the physiologically tolerated salts thereof, have an improved spectrum of action.

Preferred compounds of the formula I are those where R is —$CONH_2$, sulfo —$CO_2R^1$, —$C(O)NR^1OR^1$ or —$SO_2R^2$, with very particular preference being given to the meaning of hydrogen for $R^1$ and of methyl or ethyl for $R^2$.

The compounds of the formula I in which R is hydrogen or nitro have already been disclosed and have in the past normally been prepared to obtain derivatives of carbonyl compounds, including β-ionone, whose physical characterization is more straightforward (cf. R. Pummerer, L. Rebmann, Ber. 66 (1933) 798+801 and E. Labo Filho et al., Makromol. Chem. 187 (1986) 1573–82). The possibility of pharmacological use described herein is surprising and novel.

The compounds of the formula I may be produced as mixtures of syn and anti or cis and trans isomers. These can be separated and isolated in pure form by, for example, solubility differences or conventional chromatographic methods. The present invention relates both to the pure isomers and to the mixtures thereof.

Both the pure isomers and mixtures thereof can be used as therapeutic or cosmetic agents.

Some of the compounds according to the invention have an acidic hydrogen and can therefore be converted with bases in a conventional manner into a physiologically tolerated salt which is readily soluble in water. Examples of suitable salts are ammonium, alkali metal salts, especially of sodium, potassium or lithium, or alkaline earth metal salts, especially of calcium or magnesium, and salts with suitable organic bases such as with lower alkylamines, e.g. methylamine, ethylamine or cyclohexylamine, or with substituted lower alkylamines, especially hydroxyl-substituted alkylamines such as diethanolamine, triethanolamine or tris(hydroxymethyl)aminomethane, and with piperidine or morpholine.

The present invention also relates to a process for the preparation of the abovementioned compounds of the formula I by condensing μ-ionone with phenylhydrazines of the formula II

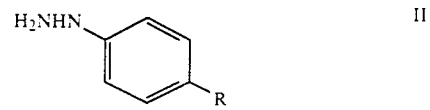

where R has the abovementioned meaning. The reaction is carried out in a conventional manner (cf. for example "Methoden der Organischen Chemie" Ed. Eugen Müller, Vol. VII, I, pp. 461–466, Thieme Verlag, Stuttgart 1954 and Vol. VII, 2b, pp. 1954–1957, Thieme Verlag, Stuttgart 1976 and Vol. X, 2, pp. 410–414, Thieme Verlag, Stuttgart 1967) in the presence or absence of a solvent or diluent or of a catalyst or of a water-binding agent at from 10° C to the boiling point of the mixture, reaction preferably being between equimolar amounts of reactants II and III or with one component in an excess of up to 15 mol-%/.

However, μ-ionone can also be employed in protected form, for example as open-chain or cyclic acetal, with acid catalysis.

The preferred solvents and diluents include hydrocarbons such as heptane, cyclohexane, toluene or xylene, as well as lower aliphatic alcohols such as methanol, ethanol and isopropanol, but also cyclohexanol and ethylene glycol, its monoalkyl and dialkyl ethers, glycerol, and ethers such as diethyl ether, diisopropyl ether and methyl tert-butyl ether or tetrahydrofuran and dioxane. Also worthy of mention are acetic acid. amides such as dimethylformamide or N-methylpyrrolidone, and pyridine, sulfolane and water or mixtures thereof.

Suitable reaction accelerators are mineral acids such as hydrochloric acid, sulfuric acid, but preferably carboxylic acids such as acetic acid and the alkali metal salts thereof. However, bases such as pyridine or morpholine can also act as catalysts.

Water-binding agents which can be used are inorganic salts such as anhydrous sodium carbonate or magnesium sulfate or else molecular sieves; if lipophilic media are used, the water formed in the reaction can be removed azeotropically.

The reaction is generally carried out under atmospheric or superatmospheric pressure.

The benzoic acid of the formula I (R=$CO_2H$) according to the invention can, if desired, be converted into other derivatives of the formula I according to the invention by first preparing an activated derivative thereof, e.g. a carbonyl halide, azide, imidazolide or anhydride, the O-acyl-N,N'-dicyclohexylurea or p-nitrophenyl ester, and reacting the latter with ammonia to give the corresponding amide (R=$CONH_2$) or else with a hydroxylamine of the formula $HNR^1OR^1$ to give the hydroxamic acid derivative (R=$CONR^1OR^1$) according to the invention. The reaction is carried out by conventional methods (cf. Jerry March, "Advanced Organic Chemistry", McGraw-Hill Kogakushu Ltd., Tokyo, 2nd Ed. 1977, pp. 384+385 and literature cited therein).

The esters of the formula I (R=$CO_2R^1$) according to the invention are preferably prepared by a method similar to that described above, by alcoholysis of the appropriate activated derivative in a conventional manner (cf. loc.cit. pp. 361-367 and literature cited therein)

μ-ionone and some of the phenylhydrazines of the formula II are commercial products, or the latter can be prepared by conventional methods for synthesizing aromatic hydrazines, for example by reduction of the corresponding diazonium compounds which can easily be prepared from aniline derivatives (cf. "Methoden der Organischen Chemie", Ed. Eugen Müler, Vol. X, 2 pp. 169-315, Thieme Verlag Stuttgart, 1967).

Typical examples of compounds according to the invention are the following, apart from the substances mentioned in the examples:

β-ionone 4-methoxyphenylhydrazone
β-ionone 4-cyanophenylhydrazone
β-ionone 4-ethylsulfonylphenylhydrazone
β-ionone 4-aminocarboxyphenylhydrazone
β-ionone 4-methylphenylhydrazone
β-ionone 4-tert-butoxyphenylhydrazone
β-ionone 4-ethoxycarbonylphenylhydrazone
β-ionone 4-sulfophenylhydrazone
β-ionone 4-isopropylsulfonylphenylhydrazone
β-ionone 4-hydroxylaminocarbonylphenylhydrazone The compounds according to the invention and their physiologically tolerated salts can, by reason of their pharmacological properties, be used for the topical and systemic therapy and prophylaxis of precanceroses and carcinomas of the skin, the mucous membranes and internal organs and for the topical and systemic therapy of acne, psoriasis and other dermatological disorders associated with pathological keratinization, especially ichthyosis Darier's disease, herpes and leukoplakia, but also eczema, vitiligo, warts, phototoxis (premature ageing) of the skin, and dry eyes and other corneopathies and for the treatment of rheumatic disorders, especially those of an inflammatory or degenerative nature and which affect joints, muscles, tendons and other parts of the locomotor system. Preferred indications are: the therapy of dermatological disorders, of skin damage caused by sunlight, and of iatrogenic skin damage, e.g. atrophy induced by corticosteroids, and the prophylactic treatment of precanceroses and tumors.

The pharmacological effects can be shown, for example, in the following tests: the compounds according to the invention abolish the keratinization which starts in hamster tracheal tissue in vitro after vitamin A deficiency. The keratinization is part of the early phase of carcinogenesis, which is inhibited by the compounds of the formula I according to the invention in a similar test in vivo after initiation by chemical compounds, by energetic radiation or after viral cell transformation. These methods are described in Cancer Res. 36 (1972) 964-972 and Nature 250 (1974) 64-66 and 253, (1975) 47-50.

In addition, the compounds according to the invention inhibit the proliferation of certain malignant cells. This method is described in J. Natl. Cancer Inst. 60 (1978) 1035-1041, Experimental Cell Research 117 (1978) 15-22 and Proc. Natl. Acad. Sci. USA 77 (1980) 2937-2940.

The antiarthritic effect of the compounds according to the invention can be determined in a conventional manner in animal experiments using the adjuvant arthritis or streptococci cell wall induced arthritis model. The dermatological activity, for example for the treatment of acne, can be demonstrated, inter alia, by the comedolytic activity and the ability to reduce the number of cysts in the rhino mouse model.

The latter method is described by L. H. Kligman et al. in the Journal of Investigative Dermatology 73 (1978) 354-358.

The dermatological activity can also be measured by the reduction in sebaceous glands and the associated diminution in sebum production by the flank organ of the hamster. This method is described by E. C. Gomez in J. Am. Dermatol. 6 (1982) 746-750.

Furthermore, it is possible to determine the reversal which can be achieved with compounds according to the invention of skin damage caused by UV light in animal models. This method is described by L. H. Kligman et al. in Connect. Tissue Res. 12, (1984) 139-150 and in the Journal of the American Academy of Dermatology 15 (1986) 779-785.

Accordingly, the invention furthermore relates to therapeutic and cosmetic agents for topical and systemic administration, which contain a compound of the formula I as active substance in addition to conventional carriers or diluents.

The agents can accordingly be administered orally, parenterally or topically. Examples of suitable formulations are uncoated or (film)coated tablets, capsules, pills, powders, solutions or suspensions, infusion or injection solutions and pastes, ointments, gels, creams, lotions, dusting powders, solutions or emulsions and sprays.

The therapeutic or cosmetic agents can contain the compounds to be used according to the invention in a concentration of 0.001 to 1%, preferably 0.001 to 0.1%, for local use, and preferably in a single dose of 0.1 to 250 mg for systemic use as a therapeutic agent, and are administered in one or more doses each day depending on the nature and severity of the disorders.

The drugs and cosmetics of the invention are produced in a conventional manner using the conventional solid or liquid carriers or diluents and the auxiliaries which are conventionally used in pharmaceutical technology to accord with the desired mode of administration and with a suitable dosage.

Appropriate tablets can be obtained, for example, by mixing the active substance with known auxiliaries, for example inert diluents such as dextrose, sugar, sorbitol, mannitol or polyvinylpyrrolidone, disintegrants, such as corn starch or alginic acid, binders such as starch or gelatin, lubricants such as magnesium stearate or talc and/or agents to achieve a depot effect, such as carboxypolymethylene, carboxymethylcellulose, cellulose acetate phthalate or polyvinyl acetate. The tablets can also be composed of several layers.

Appropriate coated tablets can be produced by coating cores, which have been produced in a similar manner to the tablets, with conventional coating agents, for example polyvinylpyrrolidone or shellac, gum arabic, talc, titanium dioxide or sugar. The coating can also be composed of several layers, it being possible to use the auxiliaries mentioned above for tablets.

Solutions or suspensions containing the active substance according to the invention can additionally contain taste corrigents such as saccharin, cyclamate or sugar as well as, for example, flavorings such as vanillin or orange extract. They can moreover contain suspending auxiliaries such as sodium carboxymethylcellulose or preservatives such as p-hydroxybenzoates. Capsules containing active substances can be produced, for example, by the active substance being mixed with an inert carrier such as lactose or sorbitol and encapsulated in gelatin capsules.

Examples of conventional ingredients of cosmetic and pharmaceutical formulations for topical use are: anionic, cationic and nonionic emulsifiers and emulsion stabilizers which can simultaneously act as bodying agents or gel formers, such as polyvinylpyrrolidone, fatty alcohols, glycerol monostearate, polyacrylic acids, cellulose derivatives and ethylene oxide/propylene oxide block polymers, solid or liquid oily components or fats of mineral, vegetable or animal origin, synthetic oily esters such as triglyceride esters and isopropyl myristate, hydrophilic components such as glycerol, polyethylene glycol and propylene glycol.

Examples of further ingredients of cosmetics are sunscreen agents, suntan agents, preservatives, antioxidants, pigments, colorants, essential oils and perfume oils, vitamins, plant extracts, collagen etc. These substances are described, for example, in the CTFA Cosmetic Ingredient Dictionary, 3rd edition, Washington 1982.

EXAMPLE 1

β-ionone 4-carboxyphenylhydrazone 9.6 g (50 mmol) of β-ionone and 7.6 g (50 mmol) of 4-carboxyphenylhydrazine were refluxed in 75 ml of ethanol for 30 min. The reaction solution was cooled, and the precipitate was filtered off, washed with ethanol and dried. 13.0 g of the title compound of melting point 197–202° C. were obtained.

EXAMPLE 2

β-ionone 4-methylsulfonylphenylhydrazone 2.5 g (13 mmol) of β-ionone and 2.5 g (13 mmol) of 4-methylsulfonylphenylhydrazine were refluxed in 40 ml of ethanol for 3 h. Evaporation of the solvent and recrystallization of the residue from n-heptane, followed by drying, provided 2.1 g of the title compound of melting point 116°–118° C.

EXAMPLES OF PHARMACEUTICAL FORMULATIONS

Example I

| Tablet containing 250 mg of active substance Composition for 1,000 tablets: | |
|---|---|
| Active substance of Example No. 2: | 250 g |
| Potato starch: | 100 g |
| Lactose: | 50 g |
| 4% gelatin solution: | 45 g |
| Talc: | 10 g |

Preparation:
The finely powdered active substance, potato starch and lactose are mixed. The mixture is moistened with about 45 g of 4% gelatin solution, converted into fine granules and dried. The dry granules are screened, mixed with 10 g of talc and compressed to tablets in a rotary tabletting machine. The tablets are packed into tightly sealed polypropylene containers.

Example II

| Cream containing 0.1% active substance | |
|---|---|
| Active substance of Example No. 1: | 0.1 g |
| Glycerol monostearate: | 10.0 g |
| Cetyl alcohol: | 4.0 g |
| Polyethylene glycol 400 stearate: | 10.0 g |
| Polyethylene glycol sorbitan monostearate: | 10.0 g |
| Propylene glycol: | 6.0 g |
| Methyl p-hydroxybenzoate: | 0.2 g |
| Demineralized water: | ad 100.0 g |

Preparation:
The very finely powdered active substance is suspended in propylene glycol and the suspension is stirred into the molten mixture of glycerol monostearate, cetyl alcohol, polyethylene glycol 400 stearate and polyethylene glycol sorbitan monostearate at 65° C. A solution of methyl p-hydroxybenzoate in water at 70° C. is emulsified into this mixture. After the cream has cooled it is homogenized in a colloid mill and packed into tubes.

Example III

| Dusting powder containing 0.1% active substance | |
|---|---|
| Active substance of Example No. 2: | 0.1 g |
| Zinc oxide: | 10.0 g |
| Magnesium oxide: | 10.0 g |
| Highly disperse silica: | 2.5 g |
| Magnesium stearate: | 1.0 g |
| Talc: | 76.4 g |

Preparation:
The active substance is micronized and mixed homogeneously with the other ingredients in an air-jet mill. The mixture is forced through a screen (mesh No. 7) and packed into polyethylene containers with a sprinkle top.

We claim:
1. A β-ionone phenylhydrazone of the formula I

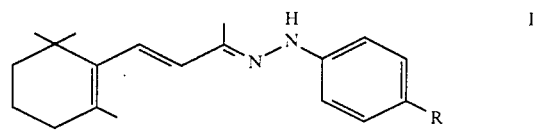

where R is $C_1$–$C_4$-alkoxy or -alkyl, cyano, sulfo, or —$CONH_2$, —$CO_2R^1$, —$C(O)NR^1OR^1$ or $S(O)_nNR^2$ (with n=0 or 2), where $R^1$ is hydrogen or $C_1$—$C_3$-alkyl, and $R^2$ is $C_1$—$C_3$-alkyl, and the physiologically tolerated salts thereof.

2. The compound of formula I as claimed in claim 1, wherein R is selected from the group consisting of —$CONH_2$, sulfo, —$CO_2R^1$, —$C(O)NR^1OR^1$ and —$SO_2R^2$.

3. The compound of the formula 1 as claimed in claim 1, in which R is selected from the group consisting of —$CONH_2$, sulfo, —$CO_2R^1$, —$C(O)NR^1OR^1$ and —$SO_2R^2$, where $R^1$ is hydrogen, and $R^2$ is selected from the group consisting of methyl and ethyl, and the physiologically tolerated salts thereof.

* * * * *